(12) United States Patent
Nagar et al.

(10) Patent No.: US 11,475,376 B2
(45) Date of Patent: Oct. 18, 2022

(54) CASCADED MACHINE LEARNING TRAVEL AGENT

(71) Applicant: INTERNATIONAL BUSINESS MACHINES CORPORATION, Armonk, NY (US)

(72) Inventors: Raghuveer Prasad Nagar, Kota (IN); Manjit Singh Sodhi, Bangalore (IN); Satyam Jakkula, Bengaluru (IN); Kshitiz Shrivastava, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 407 days.

(21) Appl. No.: 16/750,881

(22) Filed: Jan. 23, 2020

(65) Prior Publication Data

US 2021/0232979 A1    Jul. 29, 2021

(51) Int. Cl.
| | |
|---|---|
| *G06Q 10/02* | (2012.01) |
| *G06N 20/20* | (2019.01) |
| *G06N 5/04* | (2006.01) |
| *G06Q 10/04* | (2012.01) |
| *G06Q 50/30* | (2012.01) |
| *G06Q 10/10* | (2012.01) |
| *G16H 10/60* | (2018.01) |

(52) U.S. Cl.
CPC ............... *G06Q 10/02* (2013.01); *G06N 5/04* (2013.01); *G06N 20/20* (2019.01); *G06Q 10/047* (2013.01); *G06Q 10/1093* (2013.01); *G06Q 50/30* (2013.01); *G16H 10/60* (2018.01)

(58) Field of Classification Search
CPC ..................................................... G06Q 10/02
See application file for complete search history.

(56) References Cited

U.S. PATENT DOCUMENTS

| | | | |
|---|---|---|---|
| 2006/0129438 | A1 | 6/2006 | Robinson |
| 2010/0305984 | A1 | 12/2010 | Ben-Yitschak et al. |
| 2011/0307280 | A1 | 12/2011 | Mandelbaum |
| 2014/0046706 | A1 | 2/2014 | Goldstein et al. |
| 2017/0147951 | A1 | 5/2017 | Meyer et al. |

(Continued)

OTHER PUBLICATIONS

Schiaffino, Silvia, and Analía Amandi. "Building an expert travel agent as a software agent." Expert Systems with Applications 36.2 (2009): 1291-1299. (Year: 2009).*

(Continued)

*Primary Examiner* — Emmett K. Walsh
(74) *Attorney, Agent, or Firm* — Conley Rose, P.C.

(57) ABSTRACT

A system for providing a travel recommendation to a user device includes a memory having instructions therein and at least one processor in communication with the memory. The at least one processor is configured to execute the instructions to receive communications of event data from the user device and generate an event schedule based at least in part on the event data. The at least one processor is also configured to execute the instructions to receive communications of travel context data and generate, using a cascaded machine learning model, a predicted optimal travel itinerary based at least in part on the event schedule and the travel context data. The at least one processor is also configured to execute the instructions to communicate the predicted optimal travel itinerary for reception by the user device.

20 Claims, 4 Drawing Sheets

(56) References Cited

U.S. PATENT DOCUMENTS

| | | |
|---|---|---|
| 2017/0286861 A1 | 10/2017 | Kelly et al. |
| 2019/0114677 A1 | 4/2019 | Xie et al. |
| 2019/0272506 A1 | 9/2019 | Jaddangi |
| 2020/0134747 A1* | 4/2020 | Zhang ................ G06Q 30/0631 |

OTHER PUBLICATIONS

Heitz, et al., "Cascaded Classification Models: Combining Models for Holistic Scene Understanding."
Thomas, et al., "Cascaded Machine Learning Model for Efficient Hotel Recommendations from Air Travel Bookings," RecTour 2019, CEUR-WS.org/Vol-2435/paper2.pdf, Sep. 19, 2019, pp. 9-16.
Anonymously, "Predictive Analytics to Determine Optimal Travel Plan," IP.Com, IPCOM000243109D, Sep. 15, 2015, 3 pages.
Gama, et al., "Cascade Generalization," Machine Learning, vol. 41, 2000, pp. 315-343.
"Travel Itinerary," Wikipedia, https://en.wikipedia.org/wiki/Travel_itinerary, Oct. 31, 2019, 1 page.

* cited by examiner

CASCADED MACHINE LEARNING TRAVEL AGENT

BACKGROUND

The present disclosure relates generally to the field of cognitive computing and, more particularly, to artificially intelligent travel recommendation agents.

Various abilities of machines to acquire and apply knowledge and skills have been categorized as artificial intelligence ("AI"). Machine learning has been considered to be a form of AI. Machine learning has employed algorithms and statistical models that have enabled computer systems use to perform tasks based primarily on data patterns and associated inferences rather than explicit instructions.

Human travelers have often been confronted with many options associated with their journeys (e.g., modes of transport, departure times, lodging, etc.). The large numbers of factors to consider and massive amounts of associated data can be overwhelming. Machine learning presents opportunities to automatically generate travel recommendations based on vast amounts of data from a variety of sources.

SUMMARY

A method for providing a travel recommendation to a user device is disclosed. The method includes receiving communications of event data from the user device. The method also includes generating an event schedule based at least in part on the event data. The method also includes receiving communications of travel context data. The method also includes generating, using a cascaded machine learning model, a predicted optimal travel itinerary based at least in part on the event schedule and the travel context data. The method also includes communicating the predicted optimal travel itinerary for reception by the user device.

A system for providing a travel recommendation to a user device is also disclosed. The system includes a memory having instructions therein and at least one processor in communication with the memory. The at least one processor is configured to execute the instructions to receive communications of event data from the user device. The at least one processor is also configured to execute the instructions to generate an event schedule based at least in part on the event data. The at least one processor is also configured to execute the instructions to receive communications of travel context data. The at least one processor is also configured to execute the instructions to generate, using a cascaded machine learning model, a predicted optimal travel itinerary based at least in part on the event schedule and the travel context data. The at least one processor is also configured to execute the instructions to communicate the predicted optimal travel itinerary for reception by the user device.

A computer program product for providing a travel recommendation to a user device is also disclosed. The computer program product includes a computer readable storage medium having program instructions embodied therewith. The program instructions are executable by at least one processor to cause the at least one processor to receive communications of event data from the user device. The program instructions are also executable by the at least one processor to cause the at least one processor to generate an event schedule based at least in part on the event data. The program instructions are also executable by the at least one processor to cause the at least one processor to receive communications of travel context data. The program instructions are also executable by the at least one processor to cause the at least one processor to generate, using a cascaded machine learning model, a predicted optimal travel itinerary based at least in part on the event schedule and the travel context data. The program instructions are also executable by the at least one processor to cause the at least one processor to communicate the predicted optimal travel itinerary for reception by the user device.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

Figure 1:
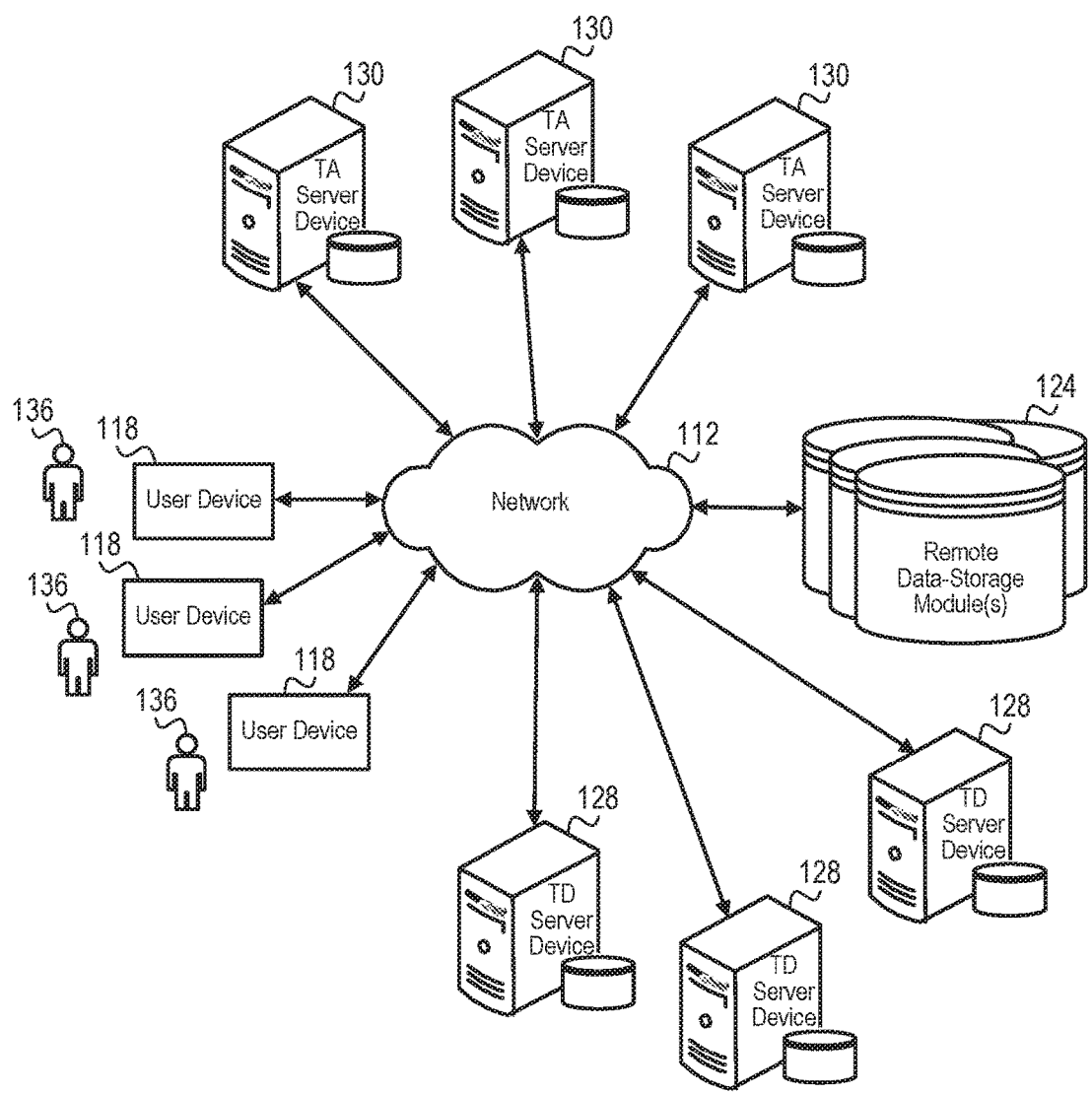
FIG. 1 is a block diagram illustration of a network environment in accordance with aspects of the present disclosure.

The illustrated figures are only exemplary and are not intended to assert or imply any limitation with regard to the environment, architecture, design, or process in which different embodiments may be implemented.

DETAILED DESCRIPTION

It should be understood at the outset that, although an illustrative implementation of one or more embodiments are provided below, the disclosed systems, computer program product, and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Aspects of the present disclosure generate an event schedule for a user based on one or more electronic calendar postings, emails, text messages, social media postings, and/or other event data regarding one or more meetings and/or other events that may require concomitant travel. In some instances, the event data may comprise one or more expressly specified, user-input times and places. Additional aspects of the present disclosure use a cascaded machine learning model to predict, based on the event schedule and based on historical and/or present travel options, travel conditions, travel preferences, and/or other travel context data, a travel itinerary having an optimally compressed predicted end-to-end travel time. Thus, aspects of the present disclosure provide an AI based system and method that predicts an optimal time taken by mode of travel at each leg of a planned journey, considering the applicable criteria for each mode. The resultant output (target) from the cascaded constituent machine learning model for each travel mode acts as an additional factor (predictor input) for the model for the next travel mode, along with the other factors for that mode. The ripple effect of travel duration is thereby factored into the cascaded machine learning model to provide personalized travel recommendations cognitively, considering the predicted target event to be attended by the user at the end of the journey.

As used within the written disclosure and in the claims, the terms "including" and "comprising" (and inflections thereof) are used in an open-ended fashion, and thus should be interpreted to mean "including, but not limited to." Unless otherwise indicated, as used throughout this document, "or" does not require mutual exclusivity, and the singular forms "a," "an," and "the" are intended to include the plural forms as well, unless the context clearly indicates otherwise.

A "module" or "unit" (and inflections thereof) as referenced herein comprises one or more hardware or electrical components such as electrical circuitry, processors, and memory that may be specially configured to perform a particular function. The memory may comprise volatile memory or non-volatile memory that stores data such as, but not limited to, computer executable instructions, machine code, and other various forms of data. The module or unit may be configured to use the data to execute one or more instructions to perform one or more tasks. In certain instances, a module or unit may also refer to a particular set of functions, software instructions, or circuitry that is configured to perform a specific task. For example, a module or unit may comprise software components such as, but not limited to, data access objects, service components, user interface components, application programming interface ("API") components; hardware components such as electrical circuitry, processors, and memory; and/or a combination thereof. As referenced herein, computer executable instructions may be in any form including, but not limited to, machine code, assembly code, and high-level programming code written in any programming language.

Also, as used herein, the term "communicate" (and inflections thereof) means to receive and/or transmit data or information over a communication link. The communication link may include both wired and wireless links, and may comprise a direct link or may comprise multiple links passing through one or more communication networks or network devices such as, but not limited to, routers, firewalls, servers, and switches. The communication networks may comprise any type of wired or wireless network. The networks may include private networks and/or public networks such as the Internet. Additionally, in some embodiments, the term communicate may also encompass internal communication between various components of a system and/or with an external input/output device such as a keyboard or display device.

FIG. 1 is a block diagram illustration of a network environment 100 in accordance with aspects of the present disclosure. The network environment 100 includes a network 112, one or more user devices 118, one or more remote data-storage modules 124, one or more travel data ("TD") server devices 128, one or more travel agent ("TA") server devices 130, and one or more users 136.

The network 112 comprises any type of network that enables the one or more user devices 118, the one or more remote data-storage modules 124, the one or more TD server devices 128, and the one or more TA server devices 130 to communicate with each other through (i.e., "over") the network 112. For example, the network 112 may comprise one or more wired and/or wireless networks such as, but not limited to, one or more radio networks (e.g., cellular network or mobile network), one or more local area networks ("LANs"), one or more wide area networks ("WANs"), one or more metropolitan area networks ("MANs"), etc. The network 112 may also comprise one or more private networks and/or one or more public networks (such as, but not limited to, the Internet). In some embodiments, the network 112 may comprise a corresponding one or more of a data processing system like the data processing system 400 (the data processing system 400 per se is not explicitly illustrated in FIG. 1, but see FIG. 4). In some embodiments, the network 112 may comprise one or more suitable computers, machines, modules, and/or devices provided by an Internet service provider.

Each of the one or more user devices 118 is communicatively coupled to the network 112 and is communicatively coupled (through or over the network 112) to each other, to the one or more remote data-storage modules 124, to the one or more TD server devices 128, and to the one or more TA server devices 130. Each of the one or more user devices 118 comprises any type of device that allows the one or more users 136 to audibly, textually, or otherwise suitably interact with the one or more TA server devices 130 through or over the network 112. Non-limiting examples of one of the one or more user devices 118 include a personal computer (desktop or laptop), a mobile device (e.g., personal digital assistant ("PDA"), smart phone, tablet, etc.), and a cognitive voice assistant device (e.g., Amazon's Alexa®, a Google Home® device, etc.). In some embodiments, the one or more user devices 118 may comprise a corresponding one or more of a data processing system like the data processing system 400 (the data processing system 400 per se is not explicitly illustrated in FIG. 1, but see FIG. 4).

Each of the one or more remote data-storage modules 124 is communicatively coupled to the network 112 and is communicatively coupled (through or over the network 112) to each other, to the one or more user devices 118, to the one or more TD server devices 128, and to the one or more TA server devices 130. The one or more remote data-storage modules 124 are configured to (alone or in combination) store and provide access to various data that may be generated, modified, and/or used in accordance with aspects of the present disclosure. In some embodiments, the one or more remote data-storage modules 124 may comprise a corresponding one or more of a data processing system like the data processing system 400 (the data processing system 400 per se is not explicitly illustrated in FIG. 1, but see FIG. 4). In some embodiments, the one or more remote data-storage modules 124 may comprise one or more suitable computers, machines, modules, and/or devices provided by an Internet service provider.

Each of the one or more TD server devices 128 is communicatively coupled to the network 112 and is communicatively coupled (through or over the network 112) to each other, to the one or more user devices 118, to the one or more remote data-storage modules 124, and to the one or more TA server devices 130. Each of the one or more TD server devices 128 comprises any type of device that can (alone or in combination with one or more other components of the network environment 100) suitably provide historical and/or present travel options, travel conditions, travel preferences, and/or other travel context data 232 that may be used in accordance with aspects of the present disclosure (the travel context data 232 per se is not explicitly called out in FIG. 1, but see FIG. 2). Non-limiting examples of the travel context data 232 include weather data, data regarding air, land, and/or water transport schedules, costs, and/or operating conditions, data regarding user preferences, and user health profile data. In some embodiments, the one or more TD server devices 128 may comprise a corresponding one or more of a data processing system like the data processing system 400 (the data processing system 400 per se is not explicitly illustrated in FIG. 1, but see FIG. 4). In some embodiments, the one or more TD server devices 128 may comprise one or more suitable computers, machines, modules, and/or devices provided by an Internet service provider, a weather service, a transportation service provider, a health services provider, a social media service, an email account/service, and/or any other suitable party or parties.

Each of the one or more TA server devices 130 is communicatively coupled to the network 112 and is communicatively coupled (through or over the network 112) to each other, to the one or more user devices 118, to the one or more remote data-storage modules 124, and to the one or more TD server devices 128. Each of the one or more TA server devices 130 comprises any type of device that can (alone or in combination with one or more other components of the network environment 100) suitably implement an artificially intelligent travel agent ("AITA") 200 in accordance with aspects of the present disclosure (the AITA 200 per se is not explicitly illustrated in FIG. 1, but see FIG. 2). In some embodiments, the one or more TA server devices 130 may comprise a corresponding one or more of a data processing system like the data processing system 400 (the data processing system 400 per se is not explicitly illustrated in FIG. 1, but see FIG. 4). In some embodiments, the one or more TA server devices 130 may comprise one or more suitable computers, machines, modules, and/or devices provided by an Internet service provider.

Figure 2:
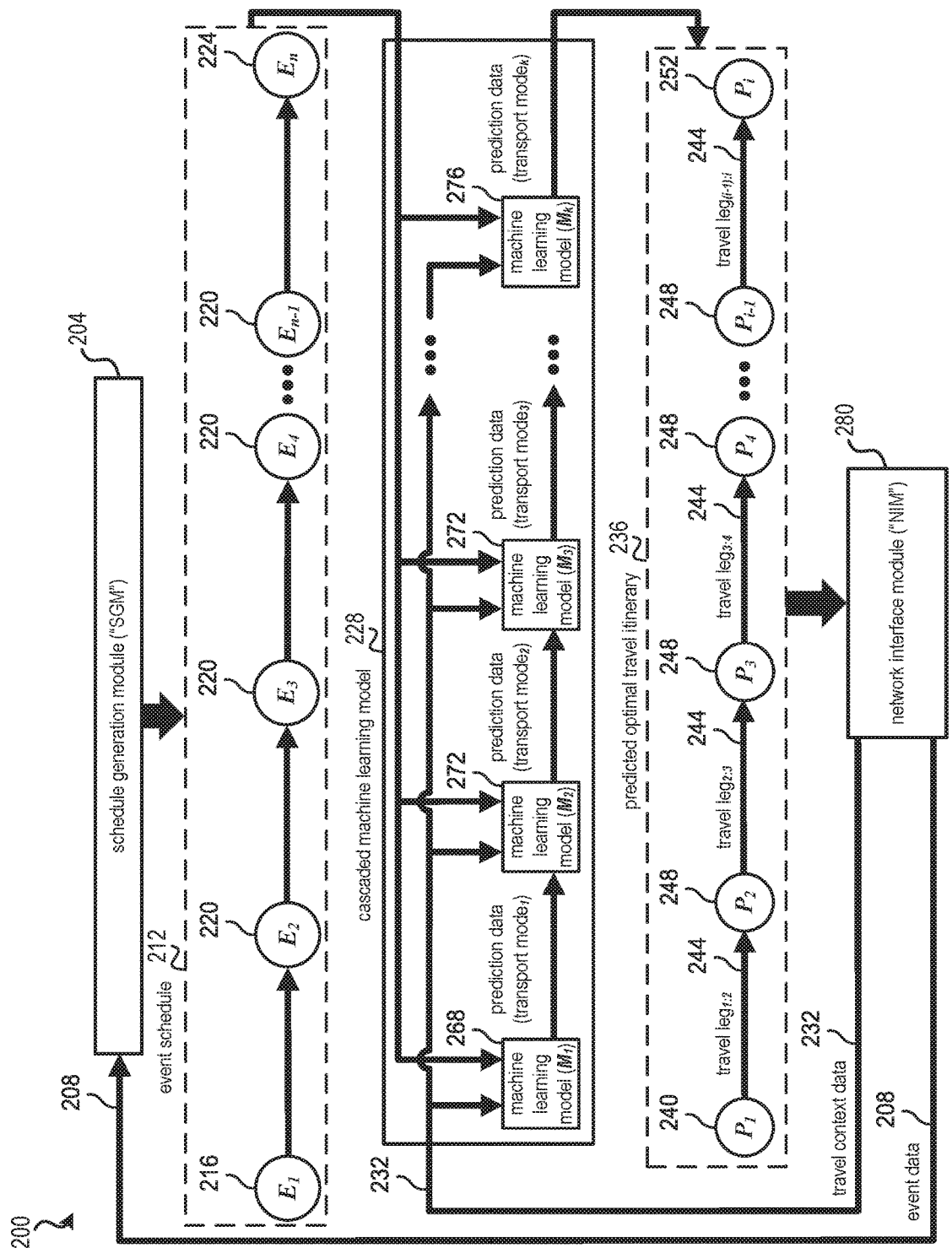
FIG. 2 is a block diagram illustration of an artificially intelligent travel agent in accordance with aspects of the present disclosure.

FIG. 2 is a block diagram illustration of the artificially intelligent travel agent ("AITA") 200 in accordance with aspects of the present disclosure. The AITA 200 is configured to implement a travel recommendation process 300 (the process 300 per se is not explicitly illustrated in FIG. 2, but see FIG. 3). The AITA 200 comprises a schedule generation module ("SGM") 204. The SGM 204 is configured to receive communications of a user's electronic calendar postings, emails, text messages, social media postings, and/or other event data 208 regarding one or more meetings and/or other events that may require concomitant travel by the user, and is also configured to generate an event schedule 212 based at least in part on the event data 208. In some instances, the event data 208 may comprise one or more expressly specified, user-input times and places. The event schedule 212 comprises time and place data corresponding to an initial event 216, corresponding to one or more intermediate events 220, and corresponding to a final event 224. For example, an electronic calendar of a user who lives and works in Austin, Tex. may have an invitation, confirmation, or other posting for a 9 am-5 pm business meeting in Armonk, N.Y. on Friday, June 12. Further, for example, the user's user device may have a text message from a business associate regarding possibly having dinner in Armonk, N.Y. on Thursday, June 11. Continuing the example, the user may have a social media account including a posting regarding the user's love of baseball and desire to one day attend a game in Yankee Stadium. And Major League Baseball may have an online game schedule showing that the Yankees will have a home game starting at 5 pm on Saturday, June 13. Additionally, the user may expressly specify that the user will need to attend a luncheon from 12 pm-2 pm on Monday, June 15 in Austin. From such event data, the SGM 204 may, determine, for example, that the event schedule 212 comprises four events: (1) an initial event (dinner) from 7 pm-9 pm in Armonk, N.Y. on Thursday, June 11; (2) a first intermediate event (meeting) from 9 am-5 pm in Armonk, N.Y. on Friday, June 12; (3) a second intermediate event (ballgame) from 5 pm-11 pm in the Bronx, N.Y. City on Saturday, June 13; and (4) a final event (luncheon) from 12 pm-2 pm in Austin on Monday, June 15.

The AITA 200 also comprises a cascaded machine learning model 228. The cascaded machine learning model 228 is communicatively coupled to, among other things, the SGM 204. The cascaded machine learning model 228 is configured to receive communications of the event schedule 212, is configured to receive communications of the travel context data 232, and is configured to generate a predicted optimal travel itinerary 236 based at least in part on the event schedule 212 and the travel context data 232. The predicted optimal travel itinerary 236 comprises time, place, and mode of travel data corresponding to a starting point ("location of origin") 240, corresponding to a plurality of travel legs 244, corresponding to one or more waypoints ("intermediate stops") 248, and corresponding to an ending point ("final destination") 252. The cascaded machine learning model 228 is configured to generate the predicted optimal travel itinerary 236 such that the predicted optimal travel itinerary 236 meets the requirements of the event schedule 112 and has an optimally compressed predicted total travel time ("end-to-end travel time") between the location of origin 240 and the final destination 252 in view of the event schedule 112 and the travel context data 232. The cascaded machine learning model 228 comprises a first constituent machine learning model 268, one or more intermediate constituent machine learning models 272, and a last constituent machine learning model 276 (collectively referred to herein as the "cascaded constituent machine learning models"). Each of the cascaded constituent machine learning models is communicatively coupled to the SGM 204 to receive communications of the event schedule 212 therefrom and is communicatively coupled to a network interface module ("NIM") 280 (described below) to receive communications of the travel context data 232 therefrom. Additionally, the cascaded constituent machine learning models are cascadedly communicatively coupled to each other and are configured to cooperate in a cascaded manner. Accordingly, the first constituent machine learning model 268 provides prediction data to a first one of the one or more intermediate constituent machine learning models 272. Further, a last one of the one or more intermediate constituent machine learning models 272 provides prediction data to the last constituent machine learning model 276. Further, each one of the remaining one or more intermediate constituent machine learning models 272 receives prediction data from a respective upstream one of the remaining one or more intermediate constituent machine learning models 272 and provides prediction to a respective downstream one of the remaining one or more intermediate constituent machine learning models 272. Each of the cascaded constituent machine learning models is also configured to generate its prediction data (based on the event schedule 212, based on the travel context data 232, and based on the prediction data that it receives from the respective upstream one of the cascaded constituent machine learning models) corresponding to optimally compressed predicted point-to-point (or "location-to-location") travel times for a respective mode of air transport, land transport, or waterborne transport that may be incorporated into the predicted optimal travel itinerary 236. For example, in some embodiments one of the cascaded constituent machine learning models may be configured to generate prediction data corresponding to the predicted fastest bus transportation that may be incorporated into the predicted optimal travel itinerary 236. Meanwhile, one or more of the cascaded constituent machine learning models may be configured to generate respective prediction data corresponding to respective ones of the predicted fastest taxicab transportation, rental car transportation, train transportation, subway transportation, bicycle transportation, scooter transportation, foot transportation, or other land transport that may be incorporated into the predicted optimal travel itinerary 236. Meanwhile, one or more of the cascaded constituent machine learning models may be configured to generate respective prediction data corresponding to respective ones of the predicted fastest airplane transportation, dirigible airship transportation, hot air balloon transportation, or other air transport that may be incorporated into the predicted optimal travel itinerary 236. Meanwhile, one or more of the cascaded constituent machine learning models may be configured to generate respective prediction data corresponding to respective ones of the predicted fastest ferryboat transportation, riverboat transportation, passenger ship transportation, or other waterborne transport that may be incorporated into the predicted optimal travel itinerary 236.

The AITA 200 also comprises the NIM 280. The NIM 280 is communicatively coupled to, among other things, the SGM 204, the cascaded machine learning model 228, and the network 112 (the network 112 per se is not explicitly illustrated in FIG. 2, but see FIG. 1). It should be appreciated that the NIM 280 is also communicatively coupled (through or over the network 112) to the one or more user devices 118, to the one or more remote data-storage modules 124, to the one or more TD server devices 128, and to the one or more TA server devices 130 (the user devices 118, the remote data-storage modules 124, the TD server devices 128, and the TA server devices 130 per se are not explicitly shown in FIG. 2, but see FIG. 1). The NIM 280 is configured to communicatively couple and act as an interface between the AITA 200 and the network 112 (and to communicatively couple—through or over the network 112—the AITA 200 to various other components of the network environment 100) in accordance with aspects of the present disclosure. Among other things, the NIM 280 conveys the event data 208 (which the NIM 280 receives through or over the network 112) from the one or more user devices 118 to the SGM 204, and the NIM 280 conveys the travel context data 232 (which the NIM 280 receives through or over the network 112) from the one or more TD server devices 128 to the cascaded machine learning model 228. In some embodiments, the NIM 280 may be a component of one of the TA server devices 130 (the TA server devices 130 per se are not explicitly shown in FIG. 2, but see FIG. 1). In some embodiments, the NIM 280 may comprise a corresponding one or more of a data processing system like the data processing system 400 (the data processing system 400 per se is not explicitly illustrated in FIG. 2, but see FIG. 4).

Figure 3:
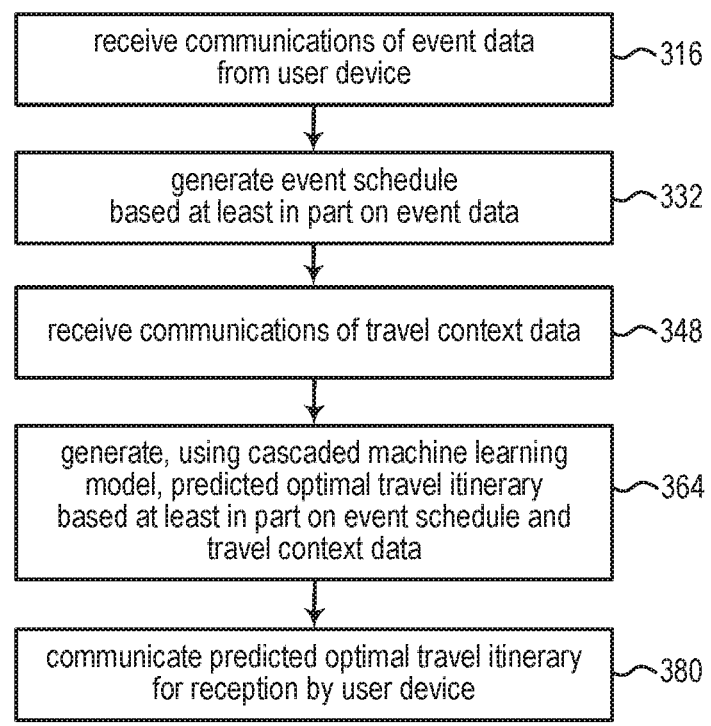
FIG. 3 is a flowchart illustration of a travel recommendation process in accordance with aspects of the present disclosure.

FIG. 3 is a flowchart illustration of the travel recommendation process 300 in accordance with aspects of the present disclosure. In some instances, one or more steps of the process 300 may be performed by the AITA 200 and/or one or more of the other systems, components, methods, and/or processes described herein. For clarity of exposition, the following description(s) of the process 300 may refer to one or more of such systems, components, methods, and/or processes. Nevertheless, it should be appreciated that the process 300 and/or any one or more of its particular steps may be performed by any suitable system(s), component(s), method(s), and/or process(es). It should also be appreciated that the process 300 may be performed concurrently or substantially concurrently with any other method(s) and/or process(es) described herein.

At step 316, the process 300 receives communications of event data from a user device. For example, in some embodiments, the NIM 280 may receive communications of the event data 208 (through or over the network 112) from the one or more user devices 118. From step 316, the process goes to (and continues at) step 332.

At step 332, the process 300 generates an event schedule based at least in part on the event data. For example, in some embodiments, the SGM 204 may generate the event schedule 212 based at least in part on the event data 208. From step 332, the process goes to (and continues at) step 348.

At step 348, the process 300 receives communications of travel context data. For example, in some embodiments, the NIM 280 may receive communications of the travel context data 232 (through or over the network 112) from the one or more TD server devices 128. From step 348, the process goes to (and continues at) step 364.

At step 364, the process 300 generates, using a cascaded machine learning model, a predicted optimal travel itinerary based at least in part on the event schedule and the travel context data. For example, in some embodiments, the cascaded machine learning model 228 may generate the predicted optimal travel itinerary 236 based at least in part on the event schedule 212 and the travel context data 232. From step 364, the process goes to (and continues at) step 380.

At step 380, the process 300 communicates the predicted optimal travel itinerary for reception by the user device. For example, in some embodiments, the NIM 280 may receive communications of the predicted optimal travel itinerary 236 from the cascaded machine learning model 228 and may in turn communicate the predicted optimal travel itinerary 236 (through or over the network 112) for reception by one of the one or more user devices 118.

Figure 4:
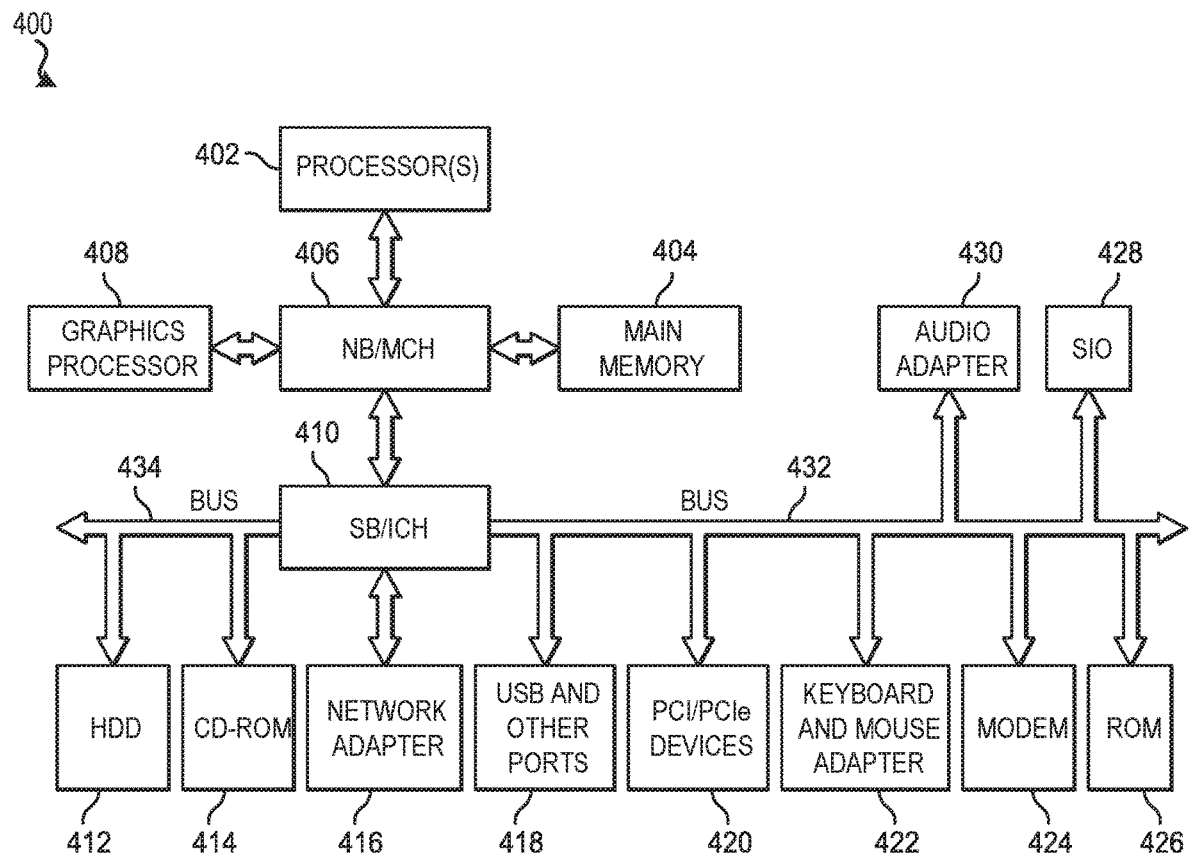
FIG. 4 is a block diagram illustration of a hardware architecture of a data processing system in accordance with aspects of the present disclosure.

FIG. 4 is a block diagram illustration of a hardware architecture of a data processing system 400 in accordance with aspects of the present disclosure. In some embodiments, one or more of the systems and/or components described herein (e.g., the network 112, the one or more user devices 118, the one or more remote data-storage modules 124, the one or more TD server devices 128, the one or more TA server devices 130, etc.) may be implemented using a corresponding one or more of the data processing system 400. Moreover, the data processing system 400 may be configured to store and execute one or more instructions of the process 300 and/or any other methods and/or processes described herein.

The data processing system 400 employs a hub architecture including north bridge and memory controller hub ("NB/MCH") 406 and south bridge and input/output ("I/O") controller hub ("SB/ICH") 410. Processor(s) 402, main memory 404, and graphics processor 408 are connected to NB/MCH 406. Graphics processor 408 may be connected to NB/MCH 406 through an accelerated graphics port ("AGP"). A computer bus, such as bus 432 or bus 434, may be implemented using any type of communication fabric or architecture that provides for a transfer of data between different components or devices attached to the fabric or architecture.

Network adapter 416 connects to SB/ICH 410. Audio adapter 430, keyboard and mouse adapter 422, modem 424, read-only memory ("ROM") 426, hard disk drive ("HDD") 412, compact disk read-only memory ("CD-ROM") drive 414, universal serial bus ("USB") ports and other communication ports 418, and peripheral component interconnect/peripheral component interconnect express ("PCI/PCIe") devices 420 connect to SB/ICH 410 through bus 432 and bus 434. PCI/PCIe devices may include, for example, Ethernet adapters, add-in cards, and personal computing ("PC") cards for notebook computers. PCI uses a card bus controller, while PCIe does not. ROM 426 may comprise, for example, a flash basic input/output system ("BIOS"). Modem 424 or network adapter 416 may be used to transmit and receive data over a network.

HDD 412 and CD-ROM drive 414 connect to SB/ICH 410 through bus 434. HDD 412 and CD-ROM drive 414 may use, for example, an integrated drive electronics ("IDE") or serial advanced technology attachment ("SATA") interface. In some embodiments, the HDD 412 may be replaced by other forms of data storage devices including, but not limited to, solid-state drives ("SSDs"). A super I/O ("SIO") device 428 may be connected to SB/ICH 410. SIO device 428 may comprise a chip on the motherboard that is configured to assist in performing less demanding controller functions for the SB/ICH 410 such as controlling a printer port, controlling a fan, and/or controlling the small light emitting diodes ("LEDS") of the data processing system 400.

The data processing system 400 may include a single processor 402 or may include a plurality of processors 402. Additionally, processor(s) 402 may have multiple cores. In some embodiments, data processing system 400 may employ a large number of processors 402 that include hundreds or thousands of processor cores. In some embodiments, the processors 402 may be configured to perform a set of coordinated computations in parallel.

An operating system is executed on the data processing system 400 using the processor(s) 402. The operating system coordinates and provides control of various components within the data processing system 400. Various applications and services may run in conjunction with the operating system. Instructions for the operating system, applications, and other data are located on storage devices, such as one or more of the HDD 412, and may be loaded into main memory 404 for execution by processor(s) 402. In some embodiments, additional instructions or data may be stored on one or more external devices. The processes described herein for the illustrative embodiments may be performed by processor(s) 402 using computer usable program code, which may be located in a memory such as, for example, main memory 404, ROM 426, or in one or more peripheral devices.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random-access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In accordance with aspects of the present disclosure, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented method, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. Further, the steps of the methods described herein may be carried out in any suitable order, or simultaneously where appropriate. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for providing a travel recommendation to a user device, the method comprising:
    obtaining historical travel data;
    training a cascaded machine learning model using the historical travel data to predict an optimal travel itinerary;
    receiving communications of event data from the user device;
    generating an event schedule based at least in part on the event data;
    receiving communications of travel context data;
    generating, using the cascaded machine learning model, a predicted optimal travel itinerary based at least in part on the event schedule and the travel context data, wherein generating, using the cascaded machine learning model, the predicted optimal travel itinerary based at least in part on the event schedule and the travel context data comprises:
        generating, using a first machine learning model corresponding to a first mode of transport, first predictions corresponding to the first mode of transport; and
        generating, based at least in part on the first predictions, using a second machine learning model corresponding to a second mode of transport, second predictions corresponding to the second mode of transport; and
    communicating the predicted optimal travel itinerary for reception by the user device.

2. The method of claim 1, wherein generating, using the cascaded machine learning model, the predicted optimal travel itinerary based at least in part on the event schedule and the travel context data further comprises:
    generating, based at least in part on the second predictions, using a third machine learning model corresponding to a third mode of transport, third predictions corresponding to the third mode of transport.

3. The method of claim 2, wherein generating, using the cascaded machine learning model, the predicted optimal travel itinerary based at least in part on the event schedule and the travel context data comprises generating the predicted optimal travel itinerary such that the predicted optimal travel itinerary has an optimally compressed predicted end-to-end travel time.

4. The method of claim 3, wherein the travel context data comprises at least some data selected from the group consisting of user preference data, health profile data, weather data, air transport data, land transport data, and waterborne transport data.

5. The method of claim 4, wherein each of the modes of transport is a type of transportation selected from the group consisting of air transport, land transport, and waterborne transport.

6. The method of claim 5, wherein one of the modes of transport is a first type of land transport and another of the modes of transport is a second type of land transport.

7. The method of claim 6, wherein at least a portion of the event data corresponds to an electronic calendar entry.

8. A system for providing a travel recommendation to a user device, the system comprising:
    a memory having instructions therein; and
    at least one processor in communication with the memory, wherein the at least one processor is configured to execute the instructions to:
        obtain historical travel data;
        train a cascaded machine learning model using the historical travel data to predict an optimal travel itinerary;
        receive communications of event data from the user device;
        generate an event schedule based at least in part on the event data;
        receive communications of travel context data;
        generate, using the cascaded machine learning model, a predicted optimal travel itinerary based at least in part on the event schedule and the travel context data, wherein generating, using the cascaded machine learning model, the predicted optimal travel itinerary based at least in part on the event schedule and the travel context data comprises:
- generating, using a first machine learning model corresponding to a first mode of transport, first predictions corresponding to the first mode of transport; and
- generating, based at least in part on the first predictions, using a second machine learning model corresponding to a second mode of transport, second predictions corresponding to the second mode of transport; and communicate the predicted optimal travel itinerary for reception by the user device.

9. The system of claim 8, wherein the at least one processor is further configured to execute the instructions to generate, based at least in part on the second predictions, using a third machine learning model corresponding to a third mode of transport, third predictions corresponding to the third mode of transport.

10. The system of claim 9, wherein the at least one processor is further configured to execute the instructions to generate the predicted optimal travel itinerary such that the predicted optimal travel itinerary has an optimally compressed predicted end-to-end travel time.

11. The system of claim 10, wherein the travel context data comprises at least some data selected from the group consisting of user preference data, health profile data, weather data, air transport data, land transport data, and waterborne transport data.

12. The system of claim 11, wherein each of the modes of transport is a type of transportation selected from the group consisting of air transport, land transport, and waterborne transport.

13. The system of claim 12, wherein one of the modes of transport is a first type of land transport and another of the modes of transport is a second type of land transport.

14. The system of claim 13, wherein at least a portion of the event data corresponds to an electronic calendar entry.

15. A computer program product for providing a travel recommendation to a user device, the computer program product comprising a computer readable storage medium having program instructions embodied therewith, the program instructions executable by at least one processor to cause the at least one processor to:
- obtain historical travel data;
- train a cascaded machine learning model using the historical travel data to predict an optimal travel itinerary;
- receive communications of event data from the user device;
- generate an event schedule based at least in part on the event data;
- receive communications of travel context data;
- generate, using the cascaded machine learning model, a predicted optimal travel itinerary based at least in part on the event schedule and the travel context data, wherein generating, using the cascaded machine learning model, the predicted optimal travel itinerary based at least in part on the event schedule and the travel context data comprises:
  - generating, using a first machine learning model corresponding to a first mode of transport, first predictions corresponding to the first mode of transport; and
  - generating, based at least in part on the first predictions, using a second machine learning model corresponding to a second mode of transport, second predictions corresponding to the second mode of transport; and
- communicate the predicted optimal travel itinerary for reception by the user device.

16. The computer program product of claim 15, wherein the program instructions are further executable by the at least one processor to cause the at least one processor to generate, based at least in part on the second predictions, using a third machine learning model corresponding to a third mode of transport, third predictions corresponding to the third mode of transport.

17. The computer program product of claim 16, wherein the program instructions are further executable by the at least one processor to cause the at least one processor to generate the predicted optimal travel itinerary such that the predicted optimal travel itinerary has an optimally compressed predicted end-to-end travel time.

18. The computer program product of claim 17, wherein the travel context data comprises at least some data selected from the group consisting of user preference data, health profile data, weather data, air transport data, land transport data, and waterborne transport data.

19. The computer program product of claim 18, wherein each of the modes of transport is a type of transportation selected from the group consisting of air transport, land transport, and waterborne transport, wherein one of the modes of transport is a first type of land transport, and wherein another of the modes of transport is a second type of land transport.

20. The computer program product of claim 19, wherein at least a portion of the event data corresponds to an electronic calendar entry.

\* \* \* \* \*